United States Patent [19]

Saito et al.

[11] Patent Number: 5,025,463
[45] Date of Patent: Jun. 18, 1991

[54] X-RAY CT SCANNER DEVICE

[75] Inventors: Yasuo Saito, Tochigi; Mitsuru Yahata, Ootawara; Kouji Honjo, Funabashi; Takayuki Matsubayashi, Tochigi, all of Japan

[73] Assignee: Kabushiki Kaisha Toshiba, Kawasaki, Japan

[21] Appl. No.: 540,601

[22] Filed: Jun. 20, 1990

[30] Foreign Application Priority Data

Jun. 21, 1989 [JP] Japan .................................. 1-158803

[51] Int. Cl.$^5$ .............................................. G01N 23/00
[52] U.S. Cl. .......................................... 378/19; 378/4; 378/901
[58] Field of Search ................... 378/19, 15, 4, 21, 22, 378/38, 99, 901

[56] References Cited

U.S. PATENT DOCUMENTS

| | | | |
|---|---|---|---|
| 4,583,241 | 4/1986 | Walters | 378/19 |
| 4,680,782 | 7/1987 | Tan et al. | 378/4 |
| 4,707,822 | 11/1987 | Hopkinson et al. | 364/414 |
| 4,712,178 | 12/1987 | Tuy et al. | 378/901 |
| 4,754,468 | 6/1988 | Mori | 378/19 |
| 4,841,553 | 6/1989 | Nagai | 378/19 |
| 4,969,166 | 11/1990 | Hahn | 378/19 |

FOREIGN PATENT DOCUMENTS

109205 5/1984 European Pat. Off. .
1587075 3/1981 United Kingdom .

Primary Examiner—Edward P. Westin
Assistant Examiner—Kim-Kwok Chu
Attorney, Agent, or Firm—Finnegan, Henderson, Farabow, Garrett and Dunner

[57] ABSTRACT

A fourth-generation X-ray CT scanner device comprises an X-ray tube for irradiating X-rays in a sector form to an object while moving on a circular orbit around the object, an annular X-ray detector array disposed coaxially with and inside the circular orbit of the X-ray tube and arranged to surround the object, for detecting the X-rays which have been irradiated from the X-ray tube and passed through the object for each channel, and a reconstruction unit for acquiring an output of the detector array to effect the reconstruction process and create a tomographic image. The X-ray array is formed of a large number of solid-state X-ray detectors and a plurality of the detectors constitute a detector module, and the array includes a large number of modules. In a displayed tomographic image, in a case where linear artifacts radiated from one point in various directions are detected, a detector module lying on an intersection (radiation point) of the artifact lines is determined as a defective detector module, and a reconstruction image is created without using output data of the defective detector module.

14 Claims, 4 Drawing Sheets

X-RAY CT SCANNER DEVICE

BACKGROUND OF THE INVENTION

1. Field of the Invention

This invention relates to an X-ray CT (Computerized Tomography) scanner device, and more particularly to a device which has a detector array including a plurality of detector modules each of which is formed of a preset number of X-ray detectors and which is constructed to prevent occurrence of a number of fine linear noises which are so-called linear artifacts caused by a breakdown of the detector module and radiated from that point on a tomographic image which corresponds to the damaged detector module.

2. Description of the Related Art

Recently, Rotates/Stationary type X-ray CT scanner devices or X-ray CT scanner devices of so-called fourth-generation type, in which a detector array having a large number of detectors is arranged over an angle of 360° around an object to completely surround the same and only an X-ray tube is rotated around the object, are frequently used. The detector array is constituted by a large number of detector modules each of which is formed of a preset number of X-ray detectors (one detector correspond to one channel) and which are arranged around the object in an annular configuration with no gap therebetween. In general, the number of detector modules constituting the detector array is more than several tens and each module has several tens of channels, and therefore the total number of channels may be several thousands.

Generally, in the X-ray CT scanner device, when one of the detectors becomes defective and X-ray projection data of a corresponding channel becomes invalid, data of the defective channel can be created by an interpolation method or the like using normal data of two adjacent channels. However, in a device such as a fourth-generation X-ray CT scanner device in which a plurality of detectors are used to constitute one detector module, if a detector module becomes defective, a plurality of successive channels are determined as defective channels, and it becomes impossible to derive data of all of the channels of one module by the interpolation method using the data of the adjacent channels. When one module becomes defective, a large number of fine linear artifacts which are radiated from that point on a tomographic image which corresponds to the defective detector module are caused on the tomographic image, and the tomographic image cannot be used for the diagnosis. For this reason, if at least one detector module becomes defective in the prior art, the entire device is treated as system-down and is not used until the module is replaced. That is, the device cannot be used for the diagnosis until the replacement or repair of the defective module is completed. If the system-down occurs in the night time, it tends to last long. However, since this type of device can be frequently used as a means for rapidly producing the result of the diagnosis in the emergency case, the long-term system-down may cause a serious problem.

SUMMARY OF THE INVENTION

An object of this invention is to provide an X-ray CT scanner device which utilizes a plurality of detector modules each constituted by a plurality of detectors and which can be prevented from being set into the system-down state and can produce a tomographic image which can be used for diagnosis without causing fine linear artifacts even if one detector module becomes defective.

The X-ray CT scanner device according to this invention comprises means for irradiating X-rays in a sector form to an object; a plurality of detector modules each having a preset number of detectors and disposed in opposition to the X-ray radiating means with the object disposed therebetween, for detecting the X-rays which have passed through the object; first reconstruction means for creating a first tomographic image based on outputs of the detector modules; means for detecting a defective detector module based on the first tomographic image; and second reconstruction means for creating a second tomographic image based on outputs of those of said detector modules which are not a defective detector module when at least one defective detector module is detected by the detecting means.

According to this invention, an X-ray CT scanner device can be provided in which X-ray projection data for each of projection angles in a range of one rotation of the X-ray radiating means around the object is first acquired to reconstruct a tomographic image and it is determined whether or not linear artifacts are present in the tomographic image. If the presence of the linear artifacts is detected, it is determined that the detector module which lies in position corresponding to a radiation point of the linear artifacts (from which a large number of artifact lines are radiated) is defective, and a tomographic image is reconstructed again based on output X-ray projection data of all the detector modules but the defective detector module so that the whole device can be prevented from being set into the system-down state even if a detector module becomes defective, thus making it possible to prevent occurrence of fine linear artifacts and provide a tomographic image which can be used for diagnosis.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently a preferred embodiment of the invention and, together with the general description given above and the detailed description of the preferred embodiments given below, serve to explain the principles of the invention.

DETAILED DESCRIPTION OF THE PREFERRED EMBODIMENTS

Figure 1:
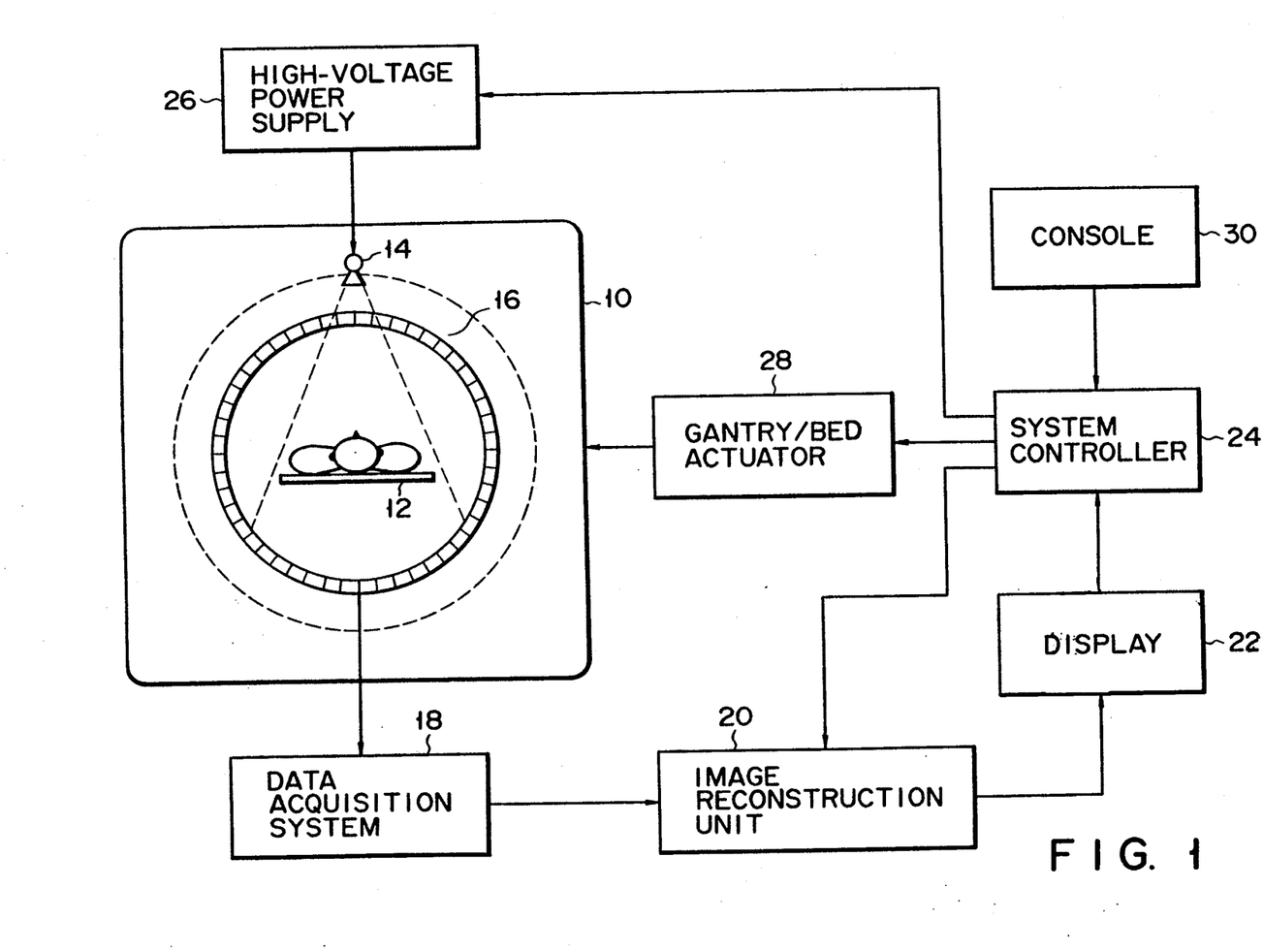
FIG. 1 is a block diagram of one embodiment of an X-ray CT scanner device according to this invention.

There will now be described an embodiment of an X-ray CT scanner device according to this invention with reference to the accompanying drawings. FIG. 1 is a block diagram showing the construction of a first embodiment. A fourth-generation X-ray CT scanner device is explained as the first embodiment, but as will be described later, this invention can also be applied to X-ray CT scanner devices of second- and succeeding-generations which utilize a plurality of detector modules each including a preset number of detectors.

A gantry 10 includes a bed 12 on which an object is laid, an X-ray tube 14 rotating around the bed 12 along a circular orbit and radiating X-rays in a sector form to the object each time it rotates through a preset angle (the angle of the X-ray tube at which the X-rays are irradiated is defined as a projection angle), and an annular X-ray detector array 16 arranged coaxially with and inside the circular orbit of the X-ray tube 14 and detecting the X-rays which have been projected from the X-ray tube 14 and passed through the object for each channel (small sector segment obtained by dividing the X-ray sector). Although not shown in the drawing, when the X-rays are irradiated from the X-ray tube 14, part of the X-ray detector array 16 is retreated from the radiation path of the X-rays so as not to disturb the X-rays. The X-ray tube 14 may be disposed not outside but inside an area defined by the X-ray detector array 16.

The X-ray detector array 16 has a large number of solid-state X-ray detectors, a preset number of detectors constitute a detector module and thus the array 16 includes a large number of detector modules. A detector signal corresponding to an amount of X-rays which has passed through the object and corresponds to each channel output of the X-ray detector array 16 is acquired as X-ray projection data by a data acquisition system 18 which has an I/V converter, integrator, multiplexer, A/D converter and the like for each channel, and the projection data is supplied to an image reconstruction unit 20 in which it is objected to a reconstruction process to produce a tomographic image, and the tomographic image thus obtained is displayed on a display unit 22.

A system controller 24 for controlling the operation of the whole device is provided, and the display unit 22, a gantry/bed actuator 28, a high-voltage power supply 26 for the X-ray tube 14 and a console 30 are connected to the system controller 24. The gantry/bed actuator 28 effects the control operation so as to synchronize the movement of the bed 10 with the irradiation of the X-rays. The high-voltage power supply 26 applies a high voltage to the X-ray tube 14 at preset timings to irradiate X-rays. The console 30 is used to give various operation instructions such as input of the scanning condition, instruction input for detecting a defective detector module as will be described later and the like to the system controller 24. The display unit 22 displays operation instructions input from the console 30 in addition to the tomographic image, thus permitting various operations to be interactively effected. The system controller 24 supplies a control signal for radiation of X-rays based on the previously set scanning condition to the high-voltage power supply 26, supplies a control signal for moving the bed and rotating the X-ray tube based on the previously set scanning condition and supplies a reconstruction control signal based on the scanning condition to the image reconstruction unit 20.

In general, the system controller 24 causes the X-ray tube 14 to rotate around the object through 360° and to irradiate X-rays for each projection angle, and supplies a control signal for reconstructing an image using X-ray projection data obtained for the entire projection angle range of 360° around the object to the image reconstruction unit 20. Further, in particular cases, the system controller 24 effects the additional control operation to rotate the X-ray tube 14 not through 360° around the object but only through a preset angle of an arc portion, or rotate the X-ray tube 14 through 360° around the object but irradiate the X-rays only in an arc portion of a preset angle. Among the above additional control operation, a control operation in which the preset angle is set to 180° +α (α is an angle of the sector of the X-rays radiated from the X-ray tube 14) is known as a half-scan method. When the system controller 24 effects the above X-ray radiation controlling operation, a reconstruction control signal which is used to effect the reconstruction process using only the projection data for the projection angle corresponding to the arc portion instead of using the projection data for the entire projection angle, for example, a reconstruction process based on the half-scan method is supplied to the image reconstruction unit 20.

Figure 2:
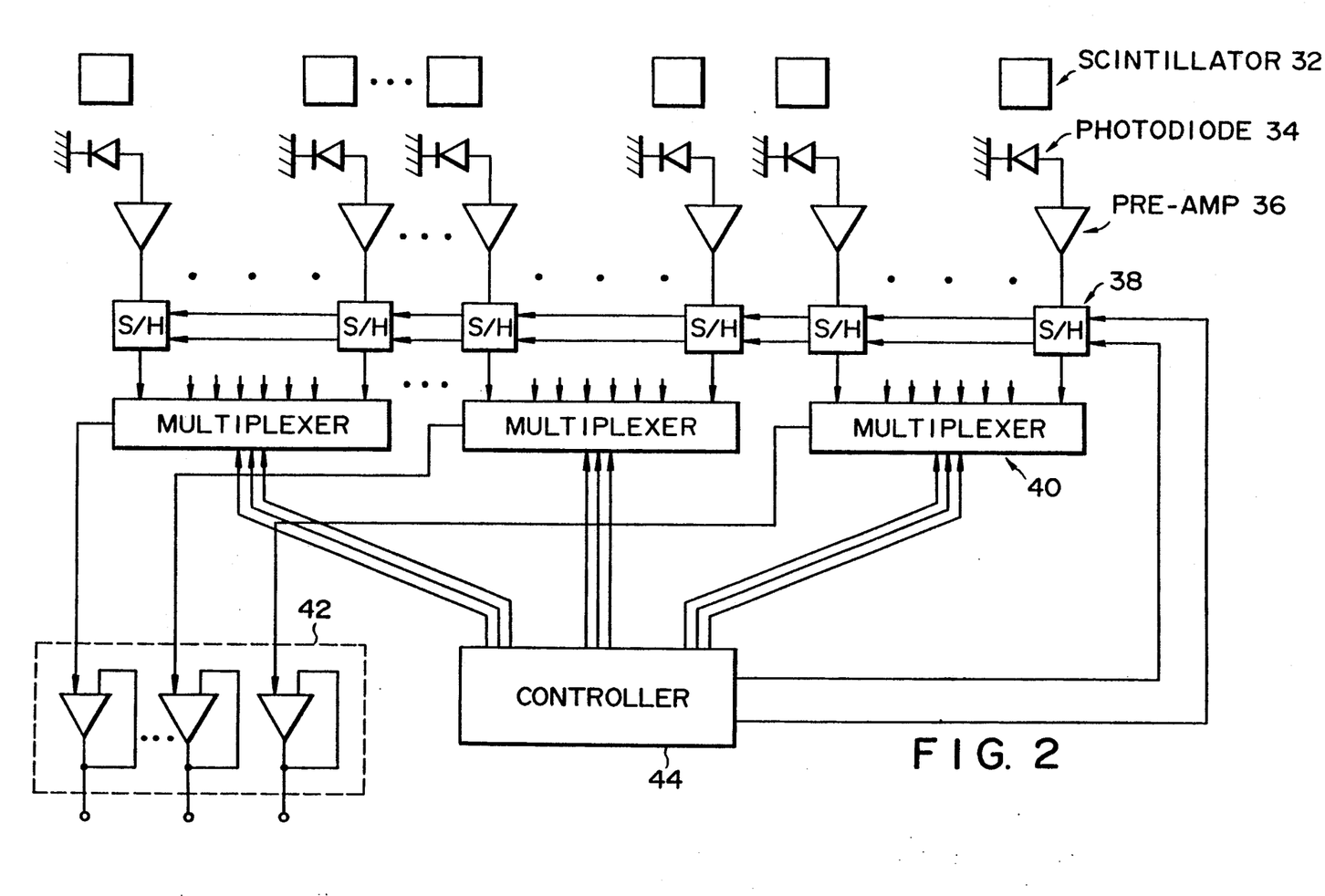
FIG. 2 is a block diagram showing the construction of an X-ray detector module and a data acquisition system of the X-ray CT scanner device.

FIG. 2 is a block diagram showing a detector array and a data acquisition system for one detector module. When the X-rays are projected onto scintillators 32 which are provided for respective channels and scintillator light generated therefrom is detected by photodiodes 34. Output signals of the photodiodes 34 are amplified by pre-amplifiers 36 and then supplied to multiplexers 40 for every predetermined number of channels via sample/hold circuits 38 having an integrating function. Outputs of the multiplexers 40 are output through a driver 42. Control signals are supplied to the multiplexers 40 and sample/hold circuits 38 from a controller 44. All of the elements of one module shown in FIG. 2 are formed on one substrate.

Figure 3:
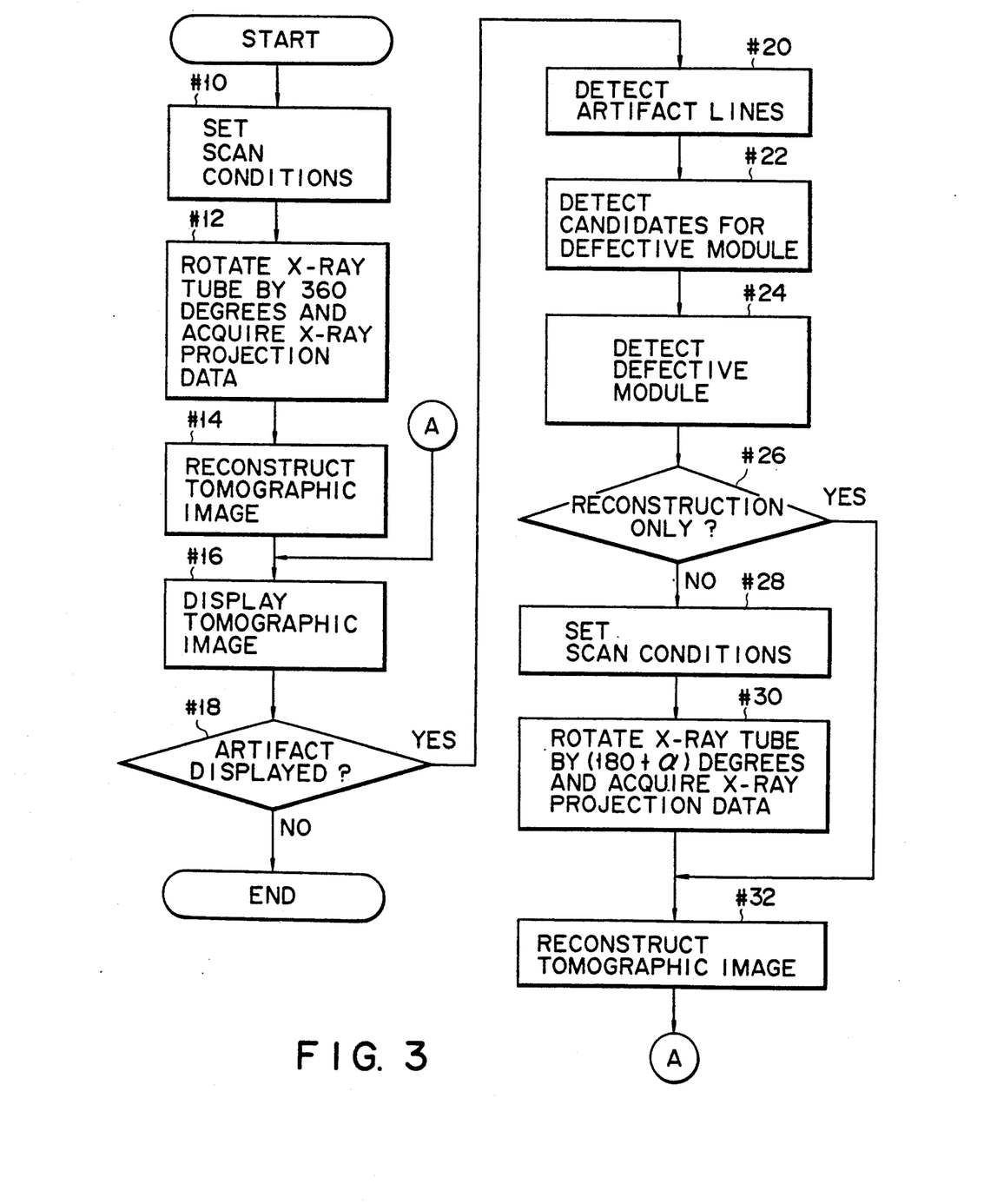
FIG. 3 is a flowchart explaining the operation of the embodiment.

Next, the operation of the embodiment is explained with reference to the flowchart shown in FIG. 3. Various scan conditions are set by an operator using the console 30 in the step #10. A scanning range, a pitch of the projection angle, radiation amount of the X-rays and the like are set as the scan conditions. At this time, the scan conditions are set such that the X-ray tube 14 is rotated around the object through 360° and X-ray projection data can be obtained for each of the projection angles in one complete rotation around the object.

In the step #12, the system controller 24 causes the gantry/bed actuator 28 to rotate the X-ray tube 14 through 360° around the object and cause the high-voltage power supply 26 to apply a high voltage to the X-ray tube 24 so as to irradiate the X-rays in a sector form to the object for each rotation of the preset angle. The X-rays which have passed through the object in each projection angle is detected by the detector array 16 and X-ray projection data given for each of the projection angles in one rotation of 360° around the object is acquired.

In the step #14, the image reconstruction unit 20 effects the image reconstruction process based on projection data obtained for all of the projection angles in one complete rotation of the X-ray tube 14 and creates a tomographic image. In this case, if projection data of a certain channel is made abnormal by a defective detector, the image reconstruction unit 20 creates data based on data of the two adjacent normal channels by using an interpolation method or the like in the same manner as in the prior art case. In the step #16, the display unit 22 displays the tomographic image thus created. A process up to this step is the same as that of an ordinary X-ray CT scanner device.

After this, it is determined based on the tomographic image displayed on the display 22 in the step #18 whether a defective detector module is present or not. If at least one detector module is defective and normal projection data is not output from the defective detector module, so-called linear artifacts which are constituted by a large number of fine lines radiated in various directions from one position (one point) corresponding to the defective detector module are present on the tomographic image. Therefore, in the step #18, the determination result made by the operator with respect to the presence or absence of the linear artifacts after observation of the tomographic image is input to the system controller 24 via the console 30.

Figure 4A:
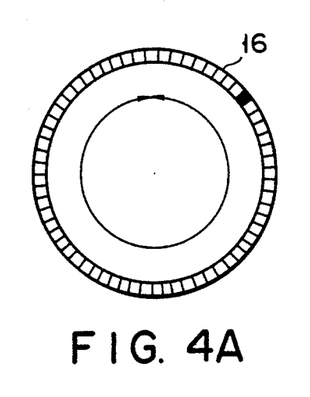
FIG. 4A is a diagram showing the scanning range in a normal case.
Figure 4B:
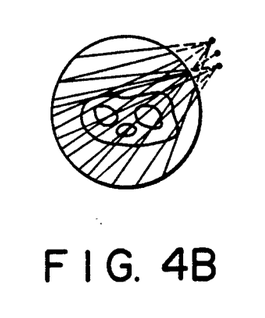
FIG. 4B is a diagram showing a tomographic image with linear artifacts.

One example of the linear artifacts is shown in FIG. 4B, and the scanning range (rotation angle of the X-ray tube 14) set at this time is shown in FIG. 4A. The detector module 16 painted black in FIG. 4A is the defective one. If no linear artifacts are present, the operation is completed as it is, and if the linear artifacts are present, the process for dealing with the defective detector module is effected in the step #20 and the succeeding steps.

Figure 5A:
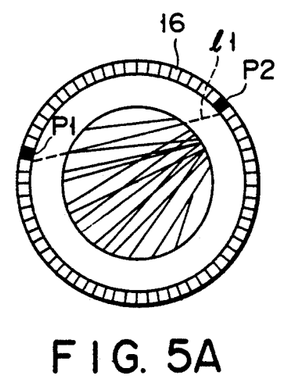
FIGS. 5A to 5C are diagrams showing the principle of detection of a defective detector module.
Figure 5B:
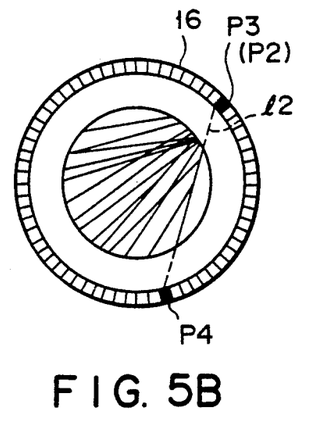
Figure 5C:
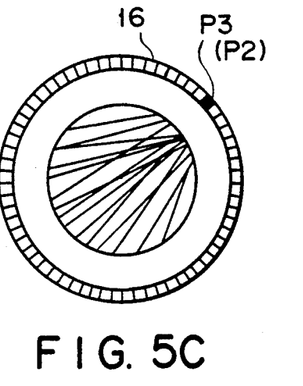

The principle of the operation of detecting a defective detector module is explained with reference to FIGS. 5A to 5C. A circle inside the detector array 16 of FIGS. 5A to 5C is a scanning circle indicating the outermost periphery of a scanning region in which a tomographic image can be obtained by scanning sectorform X-rays by one rotation of the x-ray tube 14. First, as shown in FIG. 5A, when an artifact line 11 is specified, detector modules P1 and P2 which lie at the intersections between the detector array 16 and two extended lines of the artifact line 11 extending in both directions can be determined as candidates of defective detector modules. Then, as shown in FIG. 5B, another artifact line 12 is specified and detector modules P3 and P4 which lie at the intersections between the detector array 16 and two extended lines of the artifact line 12 extending in both directions can be determined as candidates of defective detector modules in the same manner as described above. That one of the candidates of the defective detector modules which is determined as a candidate based on at least two artifact lines can be determined as a defective detector module. That is, since the defective detector module lies in position corresponding to a radiation point (from which a large number of artifact lines are radiated) of the linear artifacts, the defective detector module lies on the extended lines extending from both ends of at least two artifact lines. In the example of FIGS. 5A and 5B, the detector module P2 (=P3) is determined as a defective detector module.

In the above process, linear artifacts are first specified based on the above detection principle in the step #20. The specifying operation is effected by displaying a straight cursor on a tomographic image on the display unit 22 and moving the cursor according to the instruction from the console 30 so as to set the same on one of the artifact lines. Although not shown in the flowchart of FIG. 3, the operation of specifying the artifact line is effected until a defective detector module is detected.

In the above explanation, the determining operation in the step #18 and the specifying operation in the step #20 are effected interactively with the system controller 24 by the operator while observing an image on the display unit 22. However, it is also possible to automatically effect the above operations by detecting a linear image based on significant variation in the brightness of an image in the system controller 24.

In the step #22, detector modules lying at the intersections between the detector array 16 and two extended lines of each artifact line are detected as candidates of defective detector modules. Then, in the step #24, when at least two artifact lines are associated with a common candidate, the candidate is determined as a defective detector module. In this case, the number of defective modules detected is not limited to one but may be two or more.

As described above, when the defective detector module is detected, it becomes necessary to effect the reconstruction process for a tomographic image again, and it is determined in the step #26 whether only the reconstruction operation is effected again or the whole operation starting from the data acquisition step is effected. This is determined by the instruction input by the operator through the console 30. It is preferable to effect only the reconstruction operation when radiation amount of X-rays to the object is taken into consideration, but it is desirable to effect the whole operation starting from the data acquisition step if precise diagnosis is strongly required.

Figure 6A:
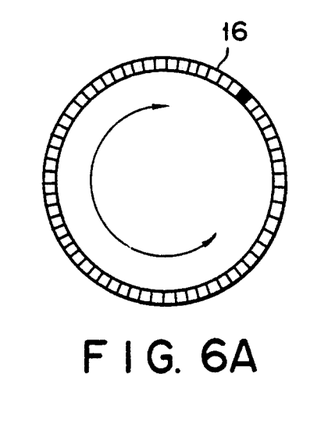
FIG. 6A is a diagram showing the scanning range in a case where a defective detector module is detected.

When an instruction that the whole operation starting from the data acquisition step is effected is input, scan conditions are set again in the step #28. The scan conditions at this time are set to effect the half-scan method without using the defective detector module as shown in FIG. 6A instead of effecting the scanning operation over the complete rotation around the object. For this purpose, in the step #30, the X-ray tube 14 is driven to rotate around the object over only an arc portion of 180° +$\alpha$ ($\alpha$ is a sector angle) which corresponds to a region having no defective detector module, and a high voltage is applied to the X-ray tube 14 from the high-voltage power supply 26 for each rotation of the preset angle to irradiate X-rays of a sector form to the object at each projection angle. In this way, X-ray projection data can be acquired by the half-scan operation of an angle (180° +$\alpha$) around the object.

In the step #32, the image reconstruction process is effected based on the reconstruction principle of the half-scan method by using the projection data thus acquired for respective arc portions to create a tomographic image. After this, the step #16 is effected again, and the image is displayed on the display unit 22 in the same manner as the first tomographic image. Therefore, if linear artifacts are present in the second tomographic image, the above-described operation is effected again.

Figure 6B:
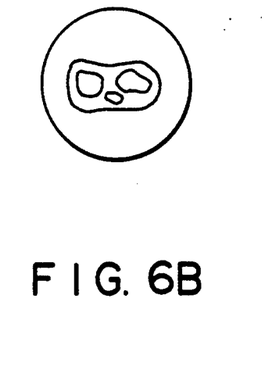
FIG. 6B is a diagram showing a tomographic image obtained when the defective detector module is detected.

Further, if an instruction that only the reconstruction is effected is input in the step #26, a tomographic image is created in the step #32 based on the half-scan principle by using half-scan data which can be obtained by excluding data corresponding to the defective detector module from all the projection data of 360° acquired in the step #12. A tomographic image obtained at this time is shown in FIG. 6B. That is, in this case, since the tomographic image is reconstructed without using an output of the defective detector module, an image including no linear artifacts can be obtained.

As described above, according to this embodiment, when a linear artifact is detected on a tomographic image, detector modules lying on the extended lines of each artifact line are determined as the candidates of defective detector modules, that one of the candidates which is associated with at least two artifact lines is determined as a defective detector module and an image reconstruction operation (for example, image reconstruction operation based on the half-scan method) is effected without using the defective detector module. Therefore, even if a detector module having a large number of detectors becomes defective, a tomographic image which has no linear artifacts and can be used for diagnosis can be obtained so that the whole device can be prevented from being set into the system-down state and the requirement for diagnosis in an emergency case can be met. Further, since projection data for the entire projection angle is acquired, half-scan data necessary for reconstruction can be selected from the acquired data without actually effecting the half-scan operation and used to reconstruct an image without irradiating the X-rays to the object again.

This invention is not limited to the above embodiment but can be applied to a third-generation device. In this case, the detector array is divided into two portions, and if a defective detector module is detected, the half-portion including the defective detector module is not used and the remaining half-portion is used as a half detector structure having only half of the detectors to effect the image reconstruction process. Further, when a defective detector module is detected, the half-scan method is used, but this is not limitative and a small-angle projection method can be used.

As described above, according to this invention, an X-ray CT scanner device can be provided which first acquires X-ray projection data in each projection angle in one complete rotation around the object to create a tomographic image, determines whether linear artifacts of fine lines is present or not, determines a detector module corresponding in position to a radiation point of artifact lines as a defective detector module if the artifact is present, and creates a tomographic image again based on output X-ray projection data of the detector modules except the defective detector module, so that the whole device can be prevented from being set into the system-down state even if a defective detector module is present and a tomographic image having no fine linear artifacts and used for diagnosis can be obtained.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An X-ray CT scanner device comprising:
   means for irradiating X-rays in a sector form to an object;
   X-ray detection means including a plurality of detector modules each having a preset number of detectors and disposed to completely surround the object, for detecting the X-rays which have passed through the object;
   first reconstruction means for subjecting outputs of all of said detector modules of said X-ray detection means to a reconstruction process to create a first tomographic image;
   means for detecting a defective detector module based on the first tomographic image created by said first reconstruction means; and
   means for subjecting outputs of those of said detector modules which are not a defective detector module to a reconstruction process to create a second tomographic image when the at least one defective detector module is detected.

2. A device according to claim 1, in which said defective module detecting means comprises:
   means for detecting artifact lines in the first tomographic image; and
   means for detecting a detector module which lies in position corresponding to an intersection of a plurality of artifact lines as a defective detector module.

3. A device according to claim 2, in which said defective module detecting means comprises:
   means for displaying the first tomographic image;
   means for displaying a linear cursor on the first image displayed on said display means;
   cursor position changing means for generating a signal for changing the position of the display position of said cursor by an operation of an operator;
   means for determining detector modules lying on the extended lines extending from the ends of said cursor displayed on a first artifact line in the first tomographic image by said cursor position changing means as candidates of defective detector modules; and
   means for determining one of detector modules lying on the extended lines extending from the ends of said cursor displayed on a second artifact line in the first tomographic image by said cursor position changing means as a defective detector module when said one of the detector modules coincides with one of the candidates of said defective detector modules 4. A device according to claim 1, in which said first reconstruction means comprises:
   means for rotating the X-ray irradiating means around the object;
   means for irradiating the X-rays when the X-ray irradiating means is at each of projection angles;
   means for acquiring X-ray projection data of each projection angle; and
   means for creating the first tomographic image based on the acquired data.

5. A device according to claim 4, in which said second reconstruction means comprises:
   means for acquiring X-ray projection data of projection angles in a range of the sum of an angle corresponding to one-half rotation around the object and an angle of the sector of the radiated X-ray; and
   means for creating the first tomographic image based on the acquired data.

6. A device according to claim 1, in which said second reconstruction means comprises:
   means for rotating the X-ray irradiating means only in a range of the sum of an angle corresponding to one-half rotation around the object and an angle of the sector of the radiated X-rays, means for irradiating the X-rays when the X-ray irradiating means is at each of projection angles in the range of the sum of the angle corresponding to one-half rotation around the object and the angle of the sector of the radiated X-ray;

means for acquires X-ray projection data of each of the projection angles; and means for creating the second tomographic image based on the acquired data.

7. A device according to claim 1, in which said first and second reconstruction means include means for deriving output data of a detector module which is detected to be defective by interpolation based on output data of two detector modules which are adjacent to the defective detector module and are not defective.

8. An X-ray CT scanner device comprising:
means for irradiating X-rays in a sector form to an object;
a plurality of detector modules each having a preset number of detectors and disposed in opposition to said X-ray radiation means with the object disposed therebetween, for detecting the X-rays which have passed through the object;
first reconstruction means for creating a first tomographic image based on outputs of said detector modules;
means for detecting a defective detector module based on the first tomographic image; and
second reconstruction means for creating a second tomographic image based on outputs of those of said detector modules which are not a defective detector module when at least one defective detector module is detected by said detecting means.

9. A device according to claim 8, in which said defective module detecting means comprises:
means for detecting artifact lines in the first tomographic image; and
means for detecting a detector module which lies in position corresponding to an intersection of a plurality of artifact lines as a defective detector module.

10. A device according to claim 8, in which said defective module detecting means comprises:
means for displaying the first tomographic image;
means for displaying a linear cursor on the first image displayed on said display means;
cursor position changing means for generating a signal for changing the position of the display position of said cursor by an operation of an operator;
means for determining detector modules lying on the extended lines extending from the ends of said cursor displayed on a first artifact line in the first topographic image by said cursor position changing means as candidates of defective detector modules; and
means for determining one of detector modules lying on the extended lines extending from the ends of said cursor displayed on a second artifact line in the first tomographic image by said cursor position changing means as a defective detector module when said one of the detector modules coincides with one of the candidates of said defective detector modules.

11. A device according to claim 8, in which said first and second reconstruction means include means for deriving output data of a detector module which is detected to be defective by interpolation based on output data of two detector modules which are adjacent to the defective detector module and are not defective.

12. A tomographic image creating method by use of an X-ray CT scanner device which includes an X-ray tube for irradiating X-rays in a sector form to an object and an X-ray detector array having a plurality of detector modules each including a preset number of detectors, comprising the steps of:
irradiating the X-rays when the X-ray tube is at each of projection angles while rotating the X-ray tube by one rotation around the object so as to acquire X-ray projection data for each of projection angles;
reconstructing a first tomographic image based on the acquired data and displaying the same;
displaying a linear cursor on the displayed first tomographic image;
changing the displayed position of said cursor by operating an operation member to display said cursor on a first artifact line in the first tomographic image;
determining detector modules which lie on extended lines extending from both ends of said cursor displayed on the first artifact line as candidates of defective detector modules;
displaying said cursor on a second artifact line in the first tomographic image by operating said operation member;
determining one of detector modules which lie on extended lines extending from both ends of said cursor displayed on the second artifact line as a defective detector module when said one of the detector modules coincides with one of the Candidates of said defective detector modules; and
subjecting outputs of those of said detector modules which are not a defective detector module to a reconstruction process to create a second tomographic image when at least one defective detector module is detected.

13. A method according to claim 12, in which said second reconstruction step includes a substep of reconstructing a second tomographic image based on only X-ray projection data which is included in the X-ray projection data acquired for the projection angles in one rotation around the object and which is obtained for projection angles lying in a range of the sum of an angle corresponding to one-half rotation around the object and an angle of the sector of the radiated X-ray.

14. A method according to claim 12, in which said second reconstruction step includes substeps of:
irradiating the X-ray for each turn of the preset angle while rotating said X-ray tube around the object only in a range of the sum of an angle corresponding to one-half rotation around the object and an angle of the sector of the radiated X-rays;
acquiring X-ray projection data of each of the projection angles in the range of the sum of the angle corresponding to one-half rotation around the object and the angle of the sector of the radiated X-rays; and
creating the second tomographic image based on the acquired data.

* * * * *

UNITED STATES PATENT AND TRADEMARK OFFICE
CERTIFICATE OF CORRECTION

PATENT NO. : 5,025,463
DATED : June 18, 1991
INVENTOR(S) : Yasuo SAITO et al.

It is certified that error appears in the above-identified patent and that said Letters Patent is hereby corrected as shown below:

Claim 3, column 8, line 44, after "modules" insert --.--.

Claim 10, column 9, line 56, change "topographic" to --tomographic--.

Claim 12, column 10, line 36, change "Candi-" to -- candi- --.

Signed and Sealed this

Twenty-fifth Day of May, 1993

Attest:

MICHAEL K. KIRK

Attesting Officer

Acting Commissioner of Patents and Trademarks